United States Patent
Cronin et al.

(10) Patent No.: US 11,141,583 B2
(45) Date of Patent: Oct. 12, 2021

(54) MULTI-LAYER BODY SURFACE ELECTRODES

(71) Applicant: St. Jude Medical, Cardiology Division, Inc., St. Paul, MN (US)

(72) Inventors: Sadie Jane Cronin, Plymouth, MN (US); Lawrence David Swanson, White Bear Lake, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 581 days.

(21) Appl. No.: 15/286,048

(22) Filed: Oct. 5, 2016

(65) Prior Publication Data
US 2017/0100055 A1    Apr. 13, 2017

Related U.S. Application Data

(60) Provisional application No. 62/240,017, filed on Oct. 12, 2015.

(51) Int. Cl.
*A61B 5/04* (2006.01)
*A61N 1/04* (2006.01)
(Continued)

(52) U.S. Cl.
CPC .......... *A61N 1/0492* (2013.01); *A61B 5/259* (2021.01); *A61B 5/6833* (2013.01); *A61N 1/048* (2013.01); *A61B 5/283* (2021.01); *A61B 5/6852* (2013.01); *A61B 2034/2051* (2016.02); *A61B 2562/0215* (2017.08); *A61B 2562/0217* (2017.08); *A61M 2025/0166* (2013.01)

(58) Field of Classification Search
CPC ............ A61B 5/04087; A61B 5/04085; A61B 5/6833; A61B 5/0408; A61B 5/0006; A61B 2562/0215; A61B 5/6832; A61B 5/053; A61B 5/0402; A61B 5/72; A61B 5/7203; A61B 2034/2051
USPC ....... 600/372, 382, 384–386, 391, 393, 395, 600/424, 508–509
See application file for complete search history.

(56) References Cited

U.S. PATENT DOCUMENTS

| | | | |
|---|---|---|---|
| 3,805,769 A * | 4/1974 | Sessions | A61B 5/0408 600/392 |
| 3,982,529 A * | 9/1976 | Sato | A61B 5/0408 600/392 |

(Continued)

FOREIGN PATENT DOCUMENTS

| | | |
|---|---|---|
| JP | H09131328 A | 5/1997 |
| WO | 2007096096 A2 | 8/2007 |

OTHER PUBLICATIONS

Liu et al. "Silver nanowire-composite electrodes for long-term electrocardiogram measurements". Sensors and Actuators A: Physical. Jun. 2016. (Year: 2016).*

*Primary Examiner* — Joseph A Stoklosa
*Assistant Examiner* — Brian M Antiskay
(74) *Attorney, Agent, or Firm* — Armstrong Teasdale LLP

(57) ABSTRACT

The present disclosure provides a multi-layer body surface electrode. The multi-layer body surface electrode includes a first layer having a first diameter, a second layer having a second diameter, and a third layer having a third diameter. The second layer is positioned between the first layer and the third layer, and the second diameter is smaller than the first diameter and the third diameter.

13 Claims, 7 Drawing Sheets

(51) Int. Cl.
*A61B 5/259* (2021.01)
*A61B 5/00* (2006.01)
*A61B 5/283* (2021.01)
*A61B 34/20* (2016.01)
*A61M 25/01* (2006.01)

(56) References Cited

U.S. PATENT DOCUMENTS

| | | | | |
|---|---|---|---|---|
| 3,989,035 A * | 11/1976 | Zuehlsdorff | ......... | A61B 5/0408 600/391 |
| 4,066,078 A * | 1/1978 | Berg | ................ | A61B 5/04087 600/391 |
| 4,112,941 A * | 9/1978 | Larimore | ............. | A61B 5/0416 439/153 |
| 4,270,543 A * | 6/1981 | Tabuchi | ............... | A61B 5/0408 600/396 |
| 4,274,420 A * | 6/1981 | Hymes | .................. | A61B 5/259 600/391 |
| 4,441,500 A * | 4/1984 | Sessions | ............. | A61B 5/0408 600/392 |
| 4,777,954 A * | 10/1988 | Keusch | ............... | A61B 5/0408 600/392 |
| 5,205,297 A * | 4/1993 | Montecalvo | ......... | A61B 8/4281 252/500 |
| 5,354,328 A * | 10/1994 | Doan | .................. | A61N 1/0587 607/129 |
| 5,427,096 A * | 6/1995 | Bogusiewicz | ....... | A61B 5/0416 600/394 |
| 5,674,275 A * | 10/1997 | Tang | ...................... | A61L 15/58 427/2.12 |
| 5,824,033 A * | 10/1998 | Ferrari | ............... | A61B 5/04087 607/142 |
| 6,007,836 A * | 12/1999 | Denzer | .................... | A61F 6/04 128/842 |
| 6,233,476 B1 | 5/2001 | Strommer et al. | | |
| 6,498,944 B1 | 12/2002 | Ben-Haim et al. | | |
| 6,690,963 B2 | 2/2004 | Ben-Haim et al. | | |
| 6,788,967 B2 | 9/2004 | Ben-Haim et al. | | |
| 6,950,688 B2 * | 9/2005 | Axelgaard | ............ | A61B 5/259 600/391 |
| 6,999,822 B2 * | 2/2006 | Koike | ................... | A61N 1/046 607/142 |
| 7,197,354 B2 | 3/2007 | Sobe | | |
| 7,263,397 B2 | 8/2007 | Hauck et al. | | |
| 7,386,339 B2 | 6/2008 | Strommer et al. | | |
| 8,849,393 B2 | 9/2014 | Hauck et al. | | |
| 9,067,055 B2 * | 6/2015 | Carrington | ............ | A61N 1/046 |
| 2005/0015134 A1 | 1/2005 | Carim | | |
| 2007/0088227 A1 | 4/2007 | Nishimura | | |
| 2009/0076363 A1 * | 3/2009 | Bly | ...................... | A61B 5/0205 600/372 |
| 2009/0264738 A1 * | 10/2009 | Markowitz | .......... | A61B 5/0422 600/424 |
| 2012/0253162 A1 * | 10/2012 | Jones | ..................... | A61N 1/046 600/382 |
| 2013/0138404 A1 | 5/2013 | Carbonera et al. | | |
| 2014/0088447 A1 | 3/2014 | Massarwa et al. | | |
| 2016/0058380 A1 * | 3/2016 | Lee | ........................ | A61B 5/145 600/365 |

* cited by examiner

MULTI-LAYER BODY SURFACE ELECTRODES

CROSS-REFERENCE TO RELATED APPLICATIONS

This application claims the benefit of priority to U.S. Provisional Patent Application No. 62/240,017 filed on Oct. 12, 2015, entitled "MULTI-LAYER BODY SURFACE ELECTRODES," the entire contents and disclosure of which are hereby incorporated herein by reference in their entirety.

FIELD OF DISCLOSURE

This disclosure relates to multi-layer body surface electrodes. More particularly, this disclosure relates to body surface electrodes including multiple layers of differing diameters for use in locating medical devices within a body using a medical positioning system.

BACKGROUND

Surface electrodes are known in the art as one available means for creating an electrical field inside of a patient. In some systems, when catheters are connected to a system amplifier, the system can dynamically record their impedance within the electrical field. Based upon the level of the impedance of each individual electrode, the three dimensional position of the catheter can be calculated and displayed using a medical positioning system.

At least some known surface electrodes, however, may contribute to shifts and drifts in the impedance measurements sensed by the medical positioning system, which can affect the ability of the medical positioning system to accurately localize the medical devices within the body. In some situations, these shifts and drifts can result from folding or tenting of the surface electrode, lifting of surface electrode edges, and/or contact with perspiration at the conductive edge of the surface electrode. Further, in at least some known surface electrodes, the overall size of the electrode may be of an undesirably large dimension, making it difficult to place other EKG electrodes in close proximity to localization surface electrodes.

BRIEF SUMMARY OF THE DISCLOSURE

In one embodiment, the present disclosure is directed to a multi-layer body surface electrode. The multi-layer body surface electrode includes a first layer having a first diameter, a second layer having a second diameter, and a third layer having a third diameter. The second layer is positioned between the first layer and the third layer, and the second diameter is smaller than the first and third diameter.

In another embodiment, the present disclosure is directed to a multi-layer body surface electrode kit. The kit includes a plurality of multi-layer body surface electrodes each including a first layer having a first diameter, a second layer having a second diameter, and a third layer having a third diameter. The second layer is positioned between the first layer and the third layer, and the second diameter is smaller than the first diameter and the third diameter. The kit also includes a respective liner attached to at least a bottom surface of the third layer of each of the plurality of electrodes.

In another embodiment, the present disclosure is directed to a medical positioning system. The medical positioning system includes a plurality of multi-layer body surface electrodes, each multi-layer body surface electrode including a first layer having a first diameter and including adhesive foam configured to adhere to a patient's skin at least on a bottom surface thereof, a second layer having a second diameter, and a third layer having a third diameter wherein the second diameter is smaller than the first diameter and the third diameter, and wherein the second layer is positioned between the first layer and the third layer. The system further includes a plurality of cables each having a first end positioned between the first layer and second layer of each of the plurality of multi-layer body surface electrodes, the plurality of cables configured to transmit signals from each of the multi-layer body surface electrodes, and a device coupled to a second end of each of the plurality of cables and configured to receive the signals and determine a location of a medical device within the patient based on the signals.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The disclosure provides body surface electrodes that include multiple layers of differing diameters such that a barrier is created around an electrically conductive layer. This barrier facilitates preventing impedance changes and also provides improved adhesion of the electrode to a patient's skin during use. The disclosed multi-layer body surface electrodes include a first layer having a first diameter, a second layer having a second diameter, and a third layer having a third diameter. The second layer is positioned between the first layer and the third layer and the second diameter is smaller than the first diameter and the third diameter, such that the first and third layers create a barrier around the conductive second (i.e., middle) layer to facilitate preventing impedance changes that may be caused by environmental factors. Further, because the first (i.e., top) layer has a larger diameter than the third (i.e., bottom, patient-contacting) layer, the first layer also assists in protecting the adhesive properties of the third layer so as to provide improved adhesion of the surface electrode and to further enhance the barrier created around the second layer. As such, the multi-layer body surface electrodes having varying diameters disclosed herein may provide a stronger adhesion of the electrode to the patient skin as well as prevent interactions that may cause impedance changes during use due to exposure to external environmental factors, such as moisture caused by, for example, perspiration or undesirable and unintentional shifting or movement of the surface electrode. In addition, the shape of the multiple layers, and in particular the first layer, assists in reducing the potential for folding, tenting, and "dog-earing" as compared to surface electrodes having other shapes, such as square or rectangular. Further, the multi-layer body surface electrodes described herein reduce the likelihood of drifts and shifts, and thus changes in impedance during use, while still maintaining a desirable electrode size.

Figure 1:
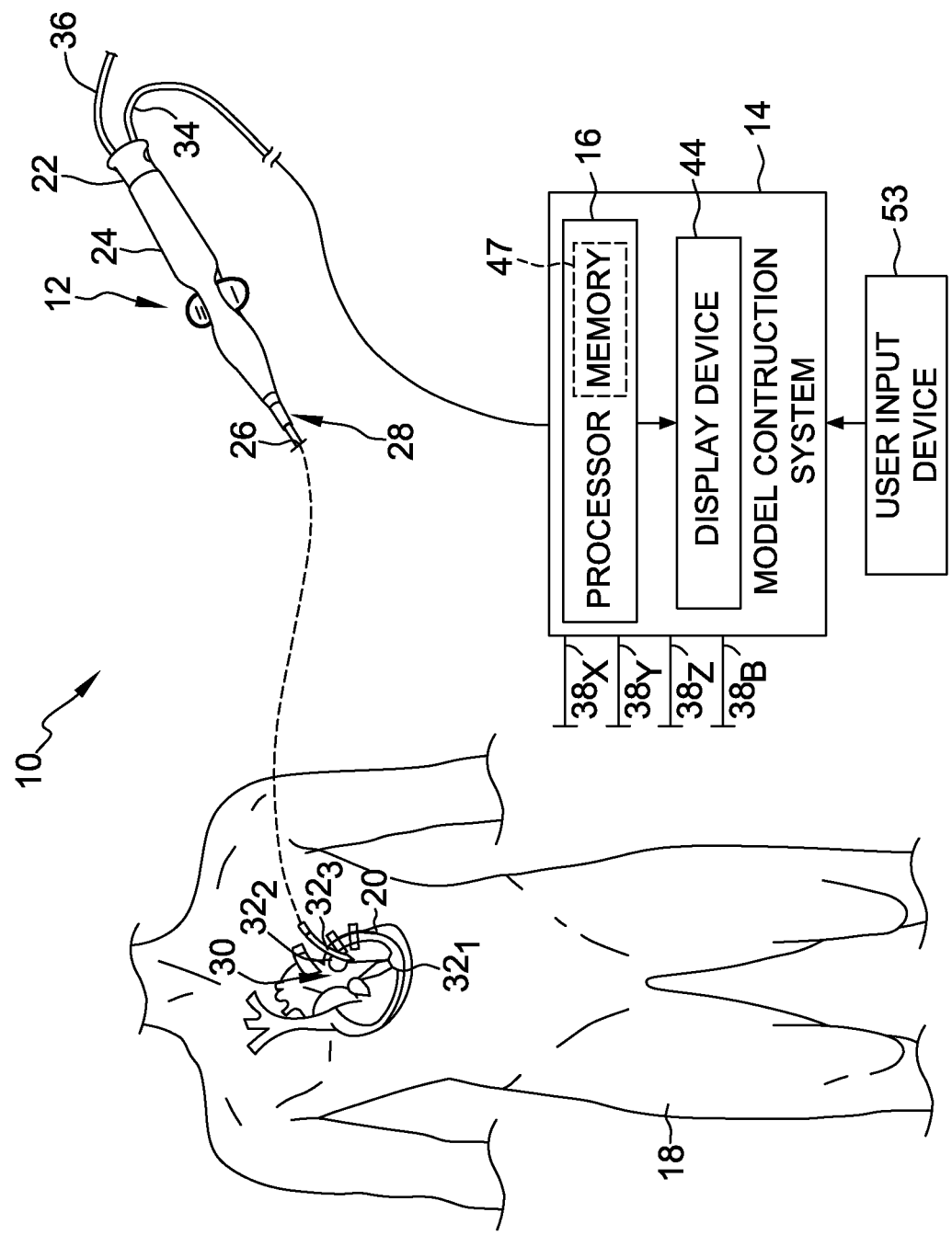
FIG. 1 is a diagrammatic view of a system for generating a multi-dimensional surface model of a geometric structure according to one embodiment.

Referring now to the drawings wherein like reference numerals are used to identify identical components in the various views, FIG. 1 illustrates one exemplary embodiment of a system 10 for generating a multi-dimensional surface model of one or more geometric structures. In this embodiment, as described herein, system 10 includes a medical positioning system for determining one or more characteristics of an electrode disposed on a medical device (e.g., a catheter) within a patient. Example medical positioning systems are generally shown and described in U.S. Pat. No. 8,849,393 entitled "Correction of Shift and Drift in Impedance-based Medical Device Navigation using Measured Impedances at External Patch Electrodes" and U.S. Pat. No. 8,517,031 entitled "System for Determining the Position of a Medical Device within a Body", the entire disclosures of which are incorporated herein by reference.

With continued reference to FIG. 1, in this embodiment, the system 10 includes, among other components, a medical device and a model construction system 14. In this embodiment, medical device is a catheter 12, and model construction system 14 includes, in part, a processing apparatus 16. Processing apparatus 16 may take the form of an electronic control unit, for example, that is configured to construct a three-dimensional model of structures within the heart using data collected by catheter 12.

As illustrated in FIG. 1, catheter 12 is configured to be inserted into a patient's body 18, and more particularly, into the patient's heart 20. Catheter 12 may include a cable connector or interface 22, a handle 24, a shaft 26 having a proximal end 28 and a distal end 30 (as used herein, "proximal" refers to a direction toward the portion of the catheter 12 near the clinician, and "distal" refers to a direction away from the clinician and (generally) inside the body of a patient), and one or more sensors 32 (e.g., $32_1$, $32_2$, $32_3$) mounted in or on shaft 26 of catheter 12. In this embodiment, sensors 32 are disposed at or near distal end 30 of shaft 26.

Connector 22 provides mechanical, fluid, and electrical connection(s) for cables, such as, for example, cables 34, 36 extending to model construction system 14 and/or other components of system 10 (e.g., the medical positioning system). Connector 22 is conventional in the art and is disposed at proximal end 28 of catheter 12, and handle 24 thereof, in particular.

Handle 24, which is disposed at proximal end 28 of shaft 26, provides a location for the clinician to hold catheter 12 and may further provide means for steering or guiding shaft 26 within body 18 of the patient.

Shaft 26 is an elongate, tubular, flexible member configured for movement within body 18. Shaft 26 supports, for example and without limitation, sensors and/or electrodes mounted thereon, such as, for example, sensors 32, associated conductors, and possibly additional electronics used for signal processing and conditioning. Shaft 26 may also permit transport, delivery, and/or removal of fluids (including irrigation fluids, cryogenic ablation fluids, and bodily fluids), medicines, and/or surgical tools or instruments.

Sensors 32 mounted in or on shaft 26 of catheter 12 may be provided for a variety of diagnostic and therapeutic purposes including, for example and without limitation, electrophysiological studies, pacing, cardiac mapping, and ablation. In this embodiment, one or more of sensors 32 are provided to perform a location or position sensing function. More particularly, and as will be described in greater detail below, one or more of sensors 32 are configured to be a positioning sensor(s) that provides information relating to the location (position and orientation) of catheter 12, and distal end 30 of shaft 26 thereof, in particular, at certain points in time. Accordingly, as catheter 12 is moved along a surface of a structure of interest of heart 20 and/or about the interior of the structure, sensor(s) 32 can be used to collect location data points that correspond to the surface of, and/or other locations within, the structure of interest. These location data points can then be used by the model positioning system to locate the medical device within the body and the model construction system 14 to generate a three-dimensional model of the structure of interest.

Model construction system 14 and the model positioning system may comprise an electric field-based system, such as, for example, the EnSite™ NavX™ system commercially available from St. Jude Medical, Inc., and generally shown with reference to U.S. Pat. No. 7,263,397 entitled "Method and Apparatus for Catheter Navigation and Location and Mapping in the Heart", the entire disclosure of which is incorporated herein by reference. In other embodiments, however, model construction system 14 and the model positioning system may comprise other types of systems, such as, for example and without limitation: a magnetic-field based system such as the Carto™ system available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; a combination electric field-based and magnetic field-based system such as the Carto 3™ System also available from Biosense Webster; as well as other impedance-based localization systems, acoustic or ultrasound-based systems, and commonly available fluoroscopic, computed tomography (CT), and magnetic resonance imaging (MRI)-based systems.

As briefly described above, sensor(s) 32 of catheter 12 include positioning sensors. Sensor(s) 32 produce signals indicative of catheter location (position and/or orientation) information. In this embodiment, wherein model construction system 14 is an electric field-based system, sensor(s) 32 may comprise one or more electrodes. Alternatively, in an embodiment where model construction system 14 is a magnetic field-based system, sensor(s) 32 may include one or more magnetic sensors configured to detect one or more characteristics of a low-strength magnetic field. For instance, in one exemplary embodiment, sensor(s) 32 may include magnetic coils disposed on or in shaft 26 of catheter 12.

For purposes of clarity and illustration, model construction system 14 will hereinafter be described as including an electric field-based system, such as, for example, the EnSite™ NavX™ system identified above.

Figure 2:
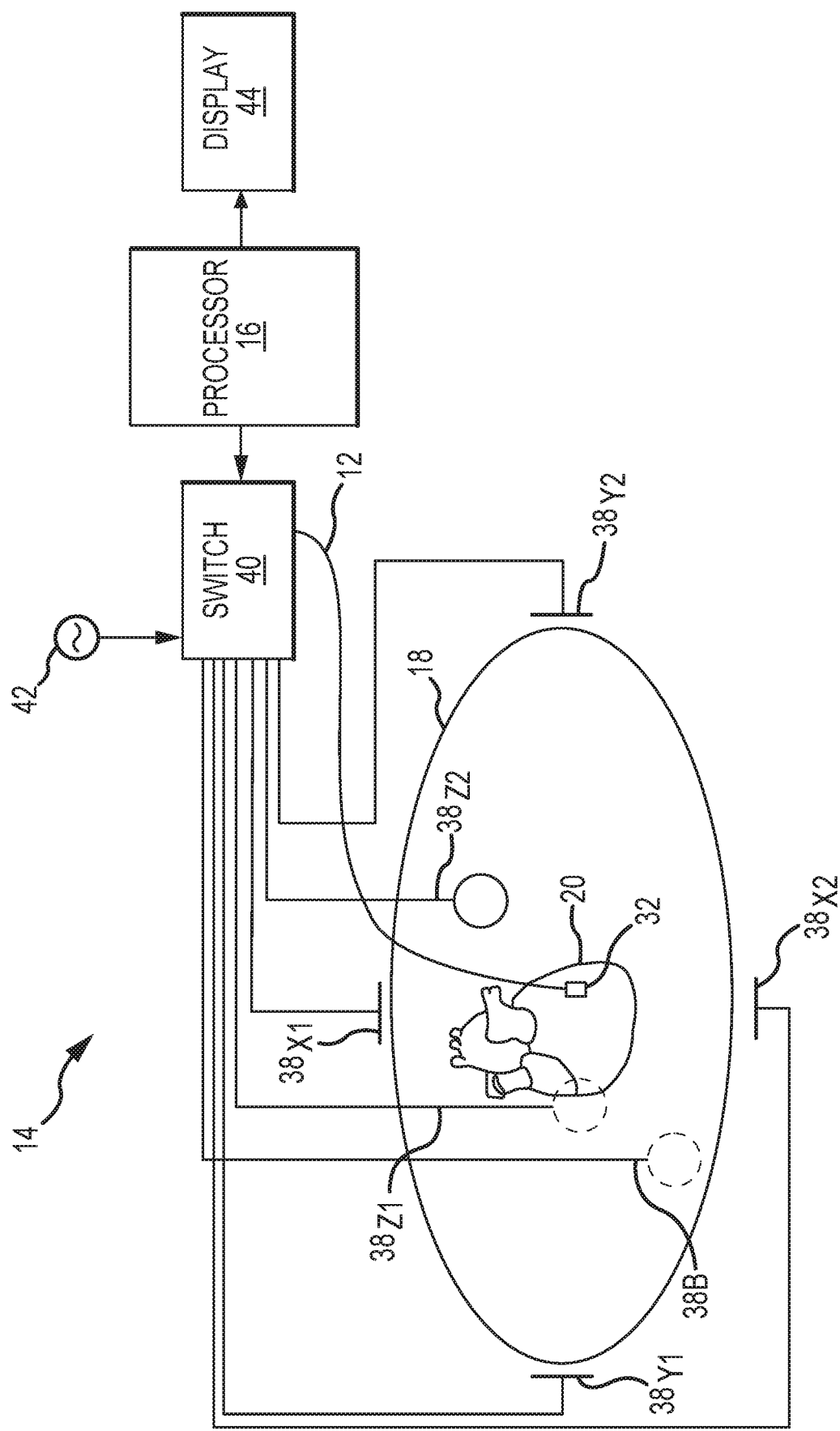
FIG. 2 is a diagrammatic and schematic view of a model construction system of the system illustrated in FIG. 1.
Figure 3A:
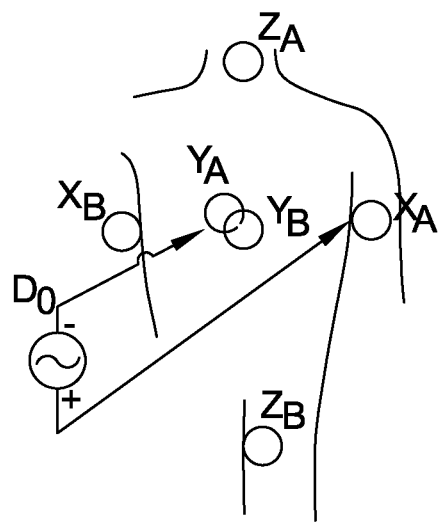
FIGS. 3A-3D are schematic diagrams of exemplary dipole pairs of driven patch electrodes suitable for use in the model construction system illustrated in FIG. 2.
Figure 3B:
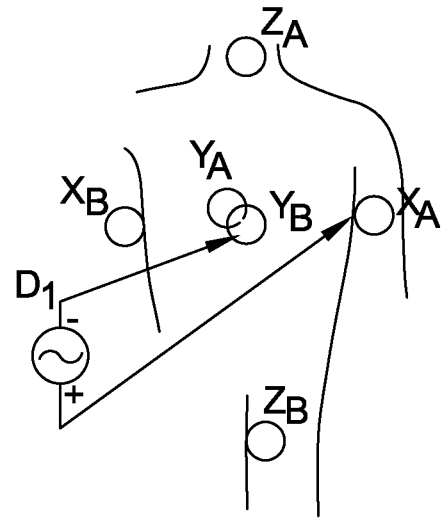
Figure 3C:
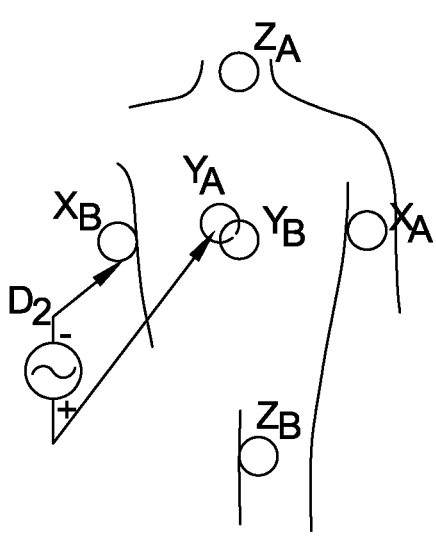
Figure 3D:
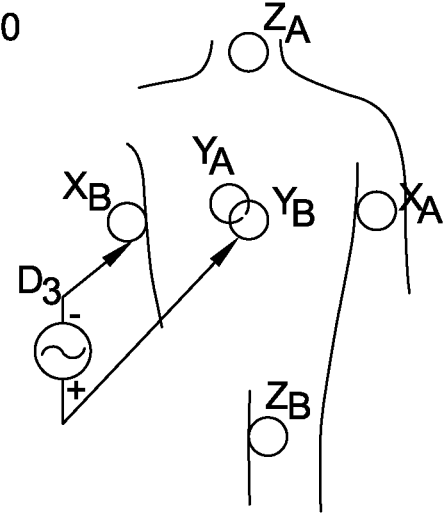

With reference to FIG. 2, in addition to the processing apparatus 16, model construction system 14 may include, among other possible components, a plurality of surface electrodes 38, a multiplex switch 40, a signal generator 42, and a display device 44. In other embodiments, some or all of these components are separate and distinct from model construction system 14 but are electrically connected to, and configured for communication with, model construction system 14.

Processing apparatus 16 may include a programmable microprocessor or microcontroller, or may include an application specific integrated circuit (ASIC). Processing apparatus 16 may include a central processing unit (CPU) and an input/output (I/O) interface through which the processing apparatus 16 may receive a plurality of input signals including, for example, signals generated by surface electrodes 38 and sensor(s) 32, and generate a plurality of output signals including, for example, those used to control and/or provide data to, for example, display device 44 and switch 40.

With the possible exception of surface electrode $38_B$ called a "belly patch," surface electrodes 38 are provided to generate electrical signals used, for example, in determining the position and orientation of catheter 12. In one embodiment, surface electrodes 38 are placed orthogonally on the surface of body 18 and are used to create axes-specific electric fields within body 18. For instance, in one embodiment surface electrodes $38_{X1}$, $38_{X2}$ may be placed along a first (x) axis. Surface electrodes $38_{Y1}$, $38_{Y2}$ may be placed along a second (y) axis, and surface electrodes $38_{Z1}$, $38_{Z2}$ may be placed along a third (z) axis. Each of surface electrodes 38 may be coupled to multiplex switch 40. In this embodiment, processing apparatus 16 is configured, through appropriate software, to provide control signals to switch 40 to thereby sequentially couple pairs of electrodes 38 to signal generator 42. Excitation of each pair of electrodes 38 generates an electric field within body 18 and within an area of interest such as heart 20. Voltage levels at non-excited electrodes 38, which are referenced to belly patch $38_B$, are filtered and converted and provided to processing apparatus 16 for use as reference values.

In this embodiment, sensor(s) 32 of catheter 12 are electrically coupled to processing apparatus 16 and are configured to serve a position sensing function. More particularly, sensor(s) 32 are placed within electric fields created in body 18 (e.g., within the heart) by exciting surface electrodes 38. For purposes of clarity and illustration only, the description below will be limited to an embodiment wherein a single sensor 32 is placed within electric fields. It will be appreciated, however, that in other embodiments that remain within the spirit and scope of the present disclosure, a plurality of sensors 32 can be placed within the electric fields and then positions and orientations of each sensor can be determined using the techniques described below.

When disposed within the electric fields, sensor 32 experiences voltages that are dependent on the location between surface electrodes 38 and the position of sensor 32 relative to tissue. Voltage measurement comparisons made between sensor 32 and surface electrodes 38 can be used to determine the location of sensor 32 relative to the tissue. Accordingly, as catheter 12 is swept about or along a particular area or surface of interest, processing apparatus 16 receives signals (location information) from sensor 32 reflecting changes in voltage levels on sensor 32 and from the non-energized surface electrodes 38. Using various known algorithms, the processing apparatus 16 may then determine the location (position and orientation) of sensor 32 and record it as a location data point corresponding to a location of sensor 32, and therefore, a point on the surface or in the interior of the structure of interest being modeled, in a memory or storage device, such as memory 47, associated with or accessible by processing apparatus 16. In some embodiments, prior to recording the location as a location data point, the raw location data represented by the signals received by processing apparatus 16 may be corrected by processing apparatus 16 to account for respiration, cardiac activity, and other artifacts using known or hereafter developed techniques. Further, locations of other portions of catheter 12 may be inferred from measurements at sensors 32, such as by interpolation or extrapolation, to generate further location data points.

While the description above has thus far been generally with respect to an orthogonal arrangement of surface electrodes 38, the present disclosure is not meant to be so limited. Rather, in other embodiments, non-orthogonal arrangements may be used to determine the location coordinates of sensor 32. For example, and in general terms, FIGS. 3A-3D depict a plurality of exemplary non-orthogonal dipoles $D_0$, $D_1$, $D_2$, and $D_3$, set in a coordinate system 50. In FIGS. 3A-3D, the X-axis patch electrodes are designated $X_A$ and $X_B$, the Y-axis patch electrodes are designated $Y_A$ and $Y_B$, and the Z-axis patch electrodes are designated $Z_A$ and $Z_B$. For any desired axis, the potentials measured across an intra-cardiac sensor, such as sensor 32, resulting from a predetermined set of drive (source sink) configurations may be combined algebraically to yield the same effective potential as would be obtained simply by driving a uniform current along the orthogonal axes. Any two of the surface electrodes $38_{X1}$, $38_{X2}$, $38_{Y1}$, $38_{Y2}$, $38_{Z1}$, and $38_{Z2}$ (See FIG. 2) may be selected as a dipole source and drain with respect to a ground reference, e.g., belly patch $38_B$, while the unexcited patch electrodes measure voltage with respect to the ground reference. Sensor 32 placed in heart 20 is also exposed to the field for a current pulse and is measured with respect to ground (e.g., belly patch $38_B$).

In another exemplary embodiment, multiple surface electrodes 38 may be arranged linearly along a common axis. In such an embodiment, excitation of an electrode pair comprising one of surface electrodes 38 and an electrode mounted on catheter 12 generates an electric field. The non-excited surface electrodes 38 may then measure potentials that can be used to determine the position of sensor 32. Accordingly, in such an embodiment, the excitation of multiple electrode pairs comprising different surface electrodes 38 and the catheter-mounted electrode may be used to determine the position of sensor 32.

Data sets from each of surface electrodes 38 and the sensor 32 are all used to determine the location of sensor 32 within heart 20. After the voltage measurements are made, a different pair of surface electrodes 38 is excited by the current source and the voltage measurement process of the remaining surface electrodes 38 and sensor 32 takes place. Once the location of sensor 32 is determined, and as was described above, the location may be recorded as a data point 46 in the same manner described above. In some embodiments, prior to recording the location as a location data point, the raw location data represented by the signals received by processing apparatus 16 may be corrected by processing apparatus 16 to account for respiration, cardiac activity, and other artifacts using known or hereafter developed techniques. Accordingly, it will be appreciated that any number of techniques may be used to determine locations of sensor 32 and to, therefore, collect data points corresponding thereto, each of which remains within the spirit and scope of the present disclosure.

Figure 4A:
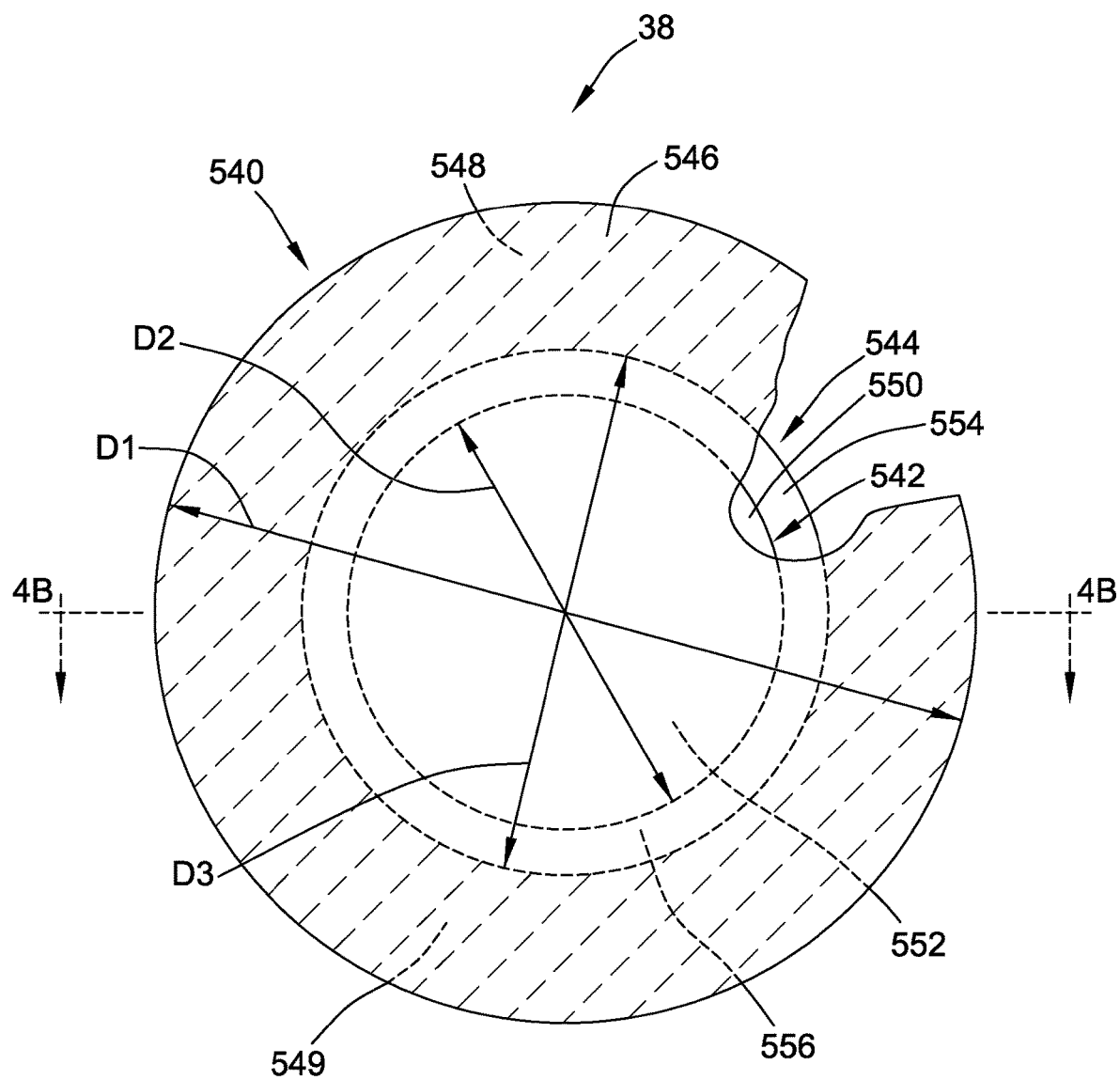
FIG. 4A is a cut-away, plan view of one embodiment of a multi-layer body surface electrode.
Figure 4B:
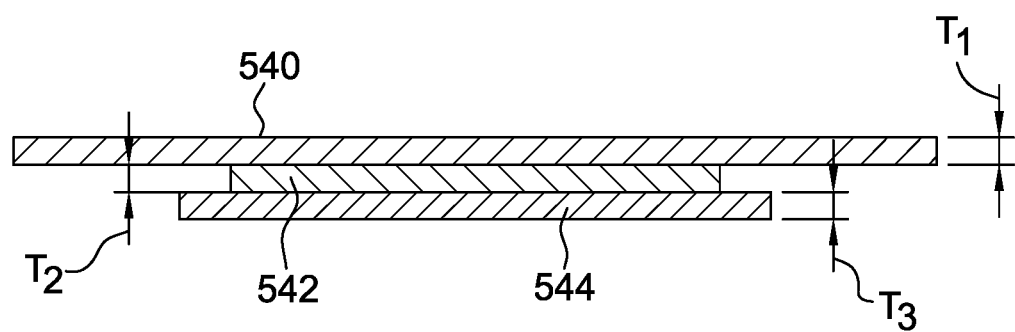
FIG. 4B is a cross-sectional view of the multi-layer body surface electrode shown in FIG. 4A and taken along line 4B-4B.

In one embodiment, surface electrodes 38 are of a multi-layer configuration including at least a first, second and third layer with varying diameters. FIGS. 4A and 4B illustrate an exemplary embodiment of a multi-layer body surface electrode. In this embodiment, surface electrode 38 includes a first layer 540 having a first diameter D1 and a first thickness T1, a second layer 542 having a second diameter D2 and a second thickness T2, and a third layer 544 having a third diameter D3 and a third thickness T3. Diameter D1 is larger than diameters D2 and D3. Further, diameter D2 is smaller than diameters D1 and D3. Accordingly, diameter D3 is larger than D2, but smaller than D1. In this embodiment, each of first, second and third layers 540, 542, and 544 are circular and are arranged concentrically with respect to one another such that second layer 542 is positioned entirely between first layer 540 and third layer 544. That is, the entire periphery of second layer 542 is positioned within the periphery of each of first layer 540 and third layer 544 such that first layer 540 and third layer 544 create a "barrier" around second layer 542. This barrier facilitates reducing the potential of impedance changes during use and improving adherence of surface electrodes 38 to the patient's skin. Further, the entire periphery of third layer 544 is positioned within the periphery of first layer 540, as will be discussed in more detail below. Although the exemplary embodiment discussed in detail herein is illustrated as including three layers, one skilled in the art will appreciate that more than three layers, such as four, five, six, or more layers, may be included in surface electrode 38 without departing from the scope of the present disclosure.

Figure 5:
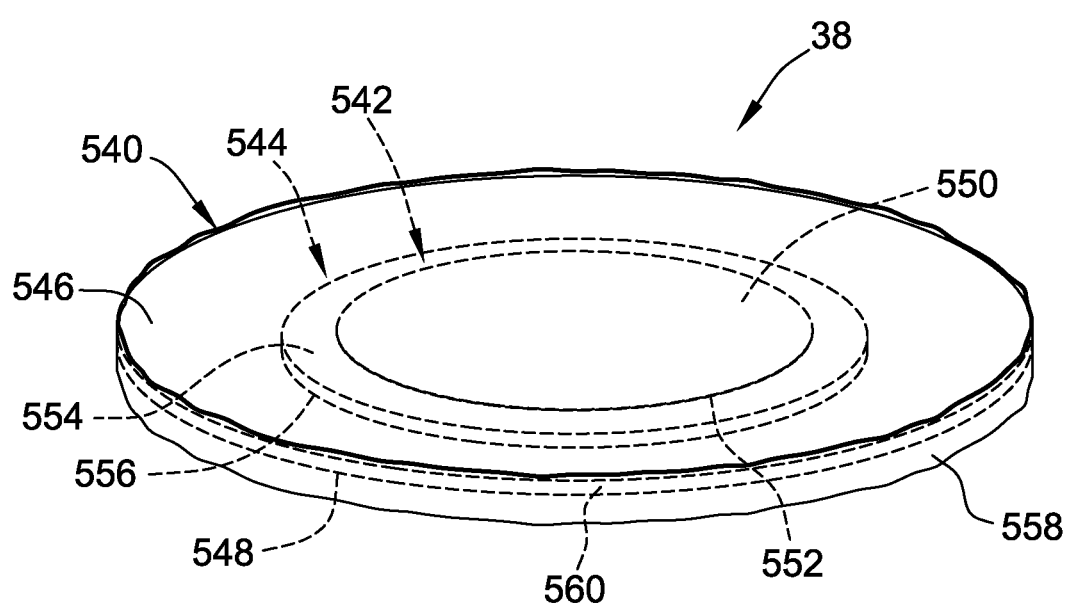
FIG. 5 illustrates the multi-layer body surface electrode of FIGS. 4A and 4B including a liner attached thereto.

As noted above, first layer 540 has a diameter D1 that is larger than each of diameters D2 and D3. First layer 540 is configured such that, during use, it is positioned within electrode 38 such that it is the farthest away from the patient's skin. That is, first layer 540 is configured such that during use, a top surface 546 of first layer 540 faces away from the patient's skin and a bottom surface 548 of first layer 540 faces toward the patient's skin. First layer 540 may be of any suitable shape and size such that it is has a larger overall cross-section and periphery than either of second layer 542 and third layer 544. That is, first layer 540 may be of any shape and size such that the entire periphery of second layer 542 and third layer 544 is contained within the periphery of first layer 540. In an exemplary embodiment shown in FIG. 5, first layer 540 is circular. Further, in this particular embodiment, for example, diameter D1 of first layer 540 may range from 2.5 inches to 4.25 inches, including but not limited to 2.5 inches to 4.0 inches, 2.5 inches to 3.5 inches, 2.5 inches to 3.0 inches, 3.0 inches to 4.0 inches, 3.0 inches to 3.5 inches, including about 2.5 inches, about 3.0 inches, about 3.5 inches, about 4.0 inches, or about 4.25 inches. First layer 540 may also have a thickness T1 of, for example, 0.034 inches. Alternatively, first layer 540 may have any suitable thickness. Although first layer 540 is illustrated in the embodiment of FIG. 5 as being circular, one skilled in the art will appreciate that first layer 540 may be of any other shape, such as oval, so long as it is commensurate with the characteristics of first layer 540 disclosed herein.

First layer 540 is comprised of an adhesive foam or tape suitable for use on and capable of adhering to a patient's skin at least on bottom surface 548 of first layer 540. In some embodiments, the adhesive foam or tape of first layer 540 is resistant to moisture, such as perspiration borne moisture.

Second layer 542 has a diameter D2 that is smaller than each of diameters D1 and D3 such that an entire periphery of second layer 542 is contained within the periphery of each of first layer 540 and third layer 544. That is, second layer 542 is configured such that it is positioned within electrode 38 between first layer 540 and third layer 544. A top surface 550 of second layer 542 contacts bottom surface 548 of first layer, and a bottom surface 552 of second layer 542 contacts a top surface 554 of third layer 544.

Second layer 542 may be of any suitable shape and size such that it is has a smaller overall cross-section than each of first layer 540 and third layer 544. That is, second layer 542 may be of any shape and size such that the entire periphery of second layer 542 is contained within the periphery of first layer 540 and third layer 544 such that a barrier to external environmental factors, such as perspiration, is created with respect to second layer 542 when applied to a patient's skin. In an exemplary embodiment shown in FIG. 5, second layer 542 is circular. Further, in this embodiment, for example, diameter D2 of second layer 542 may range from 1.3 inches to 3.05 inches, including but not limited to 1.3 inches to 3.0 inches, 1.3 inches to 2.5 inches, 1.3 inches to 2.0 inches, 2.0 inches to 3.0 inches, 2.0 inches to 2.5 inches, including about 1.3 inches, about 2.0 inches, about 2.5 inches, about 3.0 inches, or about 3.05 inches. Second layer 542 may also have a thickness T2 of, for example, 0.002 inches. Alternatively, second layer 542 may have any suitable thickness. Although second layer 542 is illustrated in the embodiment of FIG. 5 as being circular, one skilled in the art will appreciate that second layer 542 may be of any other shape, such as oval, so long as it is commensurate with the characteristics of second layer 542 disclosed herein.

Second layer 542 is comprised of an electrically conductive material suitable for receiving an electrical signal. In one particular embodiment, for example, second layer 542 is a silver carbon film.

Third layer 544 has a diameter D3 that is smaller than diameter D1 but larger than diameter D2. That is, third layer 544 is sized and configured within electrode 38 such it contacts the patient's skin during use. A top surface 554 of third layer 544 contacts bottom surface 552 of second layer 542, and a bottom surface 556 of third layer 544 contacts the patient's skin during use.

Third layer 544 may be of any suitable shape and size such that it is has a smaller overall cross-section than first layer 540 and a larger overall cross-section than second layer 542. That is, third layer 544 may be of any shape and size such that the entire periphery of third layer 544 is contained within the periphery of first layer 540, but also such that the entire periphery of second layer 542 is contained within the overall periphery of third layer 544. In other words, because diameter D1 of first layer 540 is larger than diameter D3 of third layer 544, electrode 38 is configured such that an outer portion 549 of bottom surface 548 of first layer 540 may contact the patient's skin during use, thus enhancing the barrier created by first layer 540 and third layer 544 around second layer 542. In an exemplary embodiment shown in FIG. 5, third layer 544 is circular. Further, in this embodiment, for example, diameter D3 of third layer 544 may range from 1.6 inches to 3.35 inches, including but not limited to 1.6 inches to 3.0 inches, 1.6 inches to 2.5 inches, 1.6 inches to 2.0 inches, 2.0 inches to 3.0 inches, 2.0 inches to 2.5 inches, including about 1.6 inches, about 1.8 inches, about 2.0 inches, about 2.5 inches, about 3.0 inches, or about 3.35 inches. Third layer 544 may also have a thickness T3 of, for example, 0.032 inches (e.g., when third layer 544 is 63X Hydrogel) or 0.040 inches (e.g., when third layer 544 is 63B Hydrogel). Alternatively, third layer 544 may have any suitable thickness. Although third layer 544 is illustrated in the embodiment of FIG. 5 as being circular, one skilled in the art will appreciate that third layer 544 may be of any other shape, such as oval, so long as it is commensurate with the characteristics of third layer 544 disclosed herein.

Third layer 544 is comprised of an electrically conductive adhesive suitable for adhering surface electrode 38 to the patient's skin during use. In one embodiment, for example, third layer 544 is a conductive gel. Further, first layer 540 and third layer 544 are biocompatible (e.g., to facilitate skin contact) in this embodiment.

To protect the adhesive of first layer 540 and third layer 544 from becoming damaged or impaired prior to application to a patient's skin, a liner may be applied to electrode 38. As shown in FIG. 5, liner 558 may be attached bottom surface 556 of third layer 544 and also may extend upwardly around an outer edge 560 of first layer 540. Liner 558 may be attached to bottom surface 556 and/or outer edge 560 by any conventional means known in the art and may be removed, such as by peeling liner 558 from bottom surface 556 and outer edge 560, prior to application to a patient's skin. Although illustrated in FIG. 5 as being positioned against bottom surface 556 of third layer 544 and outer edge 560 of first layer 540, it will be appreciated that in other embodiments, which remain within the spirit and scope of the present disclosure, liner 558 may be positioned against and cover additional portions of electrode 38 or may be positioned against and cover less portions of electrode 38. Liner 558 may be formed of any sufficiently pliable material suitable to remain attached or adhered to the adhesive portions of electrode 38 but sufficiently removable without damaging the adhesive properties of any portion of electrode 38.

Figure 6:
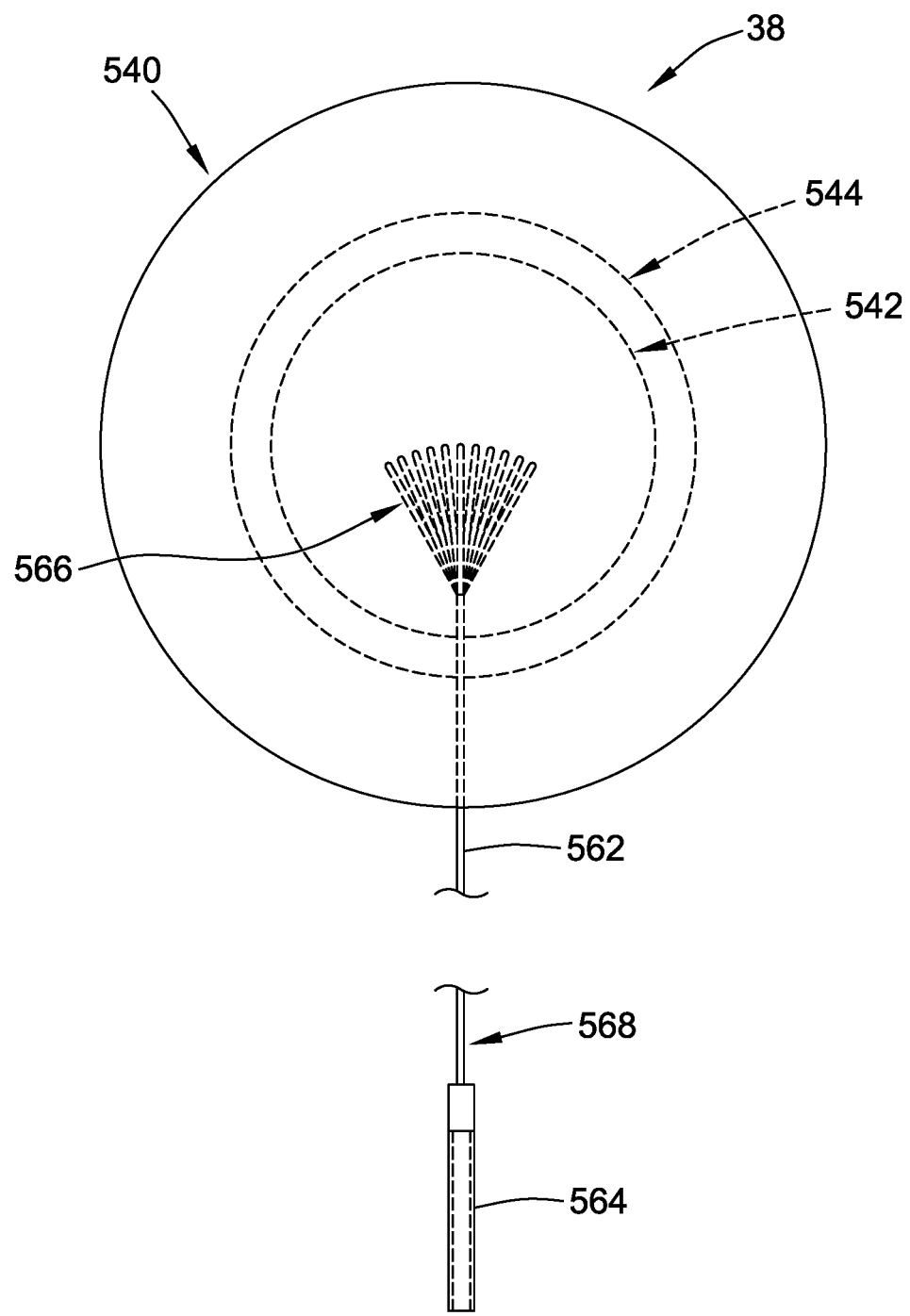
FIG. 6 illustrates one embodiment of a system including the multi-layer body surface electrode of FIGS. 4A and 4B.

Additionally, in some embodiments, a cable configured to conduct signals to and from electrode 38 (i.e., between electrode 38 and a signal generator/receiver) may be coupled between electrode 38 and the signal generator/receiver. The signal generator/receiver may be, for example signal generator 42 (shown in FIG. 2). In one embodiment, as shown in FIG. 6, cable 562 is coupled to electrode 38 such that a signal may be transmitted from electrode 38 and through cable 562 to a connector 564 that may, in some embodiments, be coupled to equipment capable of generating or receiving the electrode signals. In one particular embodiment, as shown in FIG. 6, a first end 566 of cable 562 may be splayed and adhered between first layer 540 and second layer 542 and a second end 568 of cable 562 is coupled to connector 564. It will be appreciated, however, that in other embodiments, which remain within the spirit and scope of the present disclosure, cable 562 may be coupled between electrode 38 and equipment capable of generating or receiving the electrode signals by any other known and suitable means capable of transmitting the signal from electrode 38 to the equipment.

In use, a plurality of surface electrodes 38 may be positioned on a patient as is shown, for example, in FIGS. 3A-3D. Accordingly, surface electrodes 38 may be used in system 10 (shown in FIG. 1). Alternatively, as will be appreciated by those of skill in the art, surface electrodes 38 may be used in any suitable system, and are not limited to use with the mapping systems described herein.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A multi-layer body surface electrode consisting of three flat, disk-shaped layers, the layers consisting of:
    a first layer having a first, uniform diameter and comprising a sidewall that extends between a top surface of the first layer and a continuous planar bottom surface of the first layer;
    a second layer having a second diameter and comprising an electrically conductive material, the second layer further comprising a continuous planar top surface and a continuous planar bottom surface; and
    a third layer having a third diameter and comprising an electrically conductive adhesive that forms a continuous planar top surface, wherein the second layer is positioned between the first layer and the third layer, wherein the second diameter is smaller than the first and third diameter, wherein the first diameter is larger than the third diameter, wherein the first layer continuous planar bottom surface contacts the second layer continuous planar top surface and covers the entirety of the second layer continuous planar top surface, and wherein the third layer continuous planar top surface contacts the second layer continuous planar bottom surface and covers the entirety of the second layer continuous planar bottom surface such that the electrically conductive adhesive of the third layer is in direct contact with the electrically conductive material of the second layer and also extends radially outward beyond a periphery of the electrically conductive material of the second layer;

wherein the first, second, and third layers are configured such that the first and third layers form a barrier around the second layer configured to facilitate reducing a potential of impedance changes when adhered to the patient's skin.

2. The multi-layer body surface electrode of claim 1 wherein the first layer has a first thickness that is both larger than a second thickness of the second layer and smaller than a third thickness of the third layer.

3. The multi-layer body surface electrode of claim 2 wherein the first thickness is approximately 0.034 inches, the second thickness is approximately 0.002 inches, and the third thickness is approximately 0.040 inches.

4. The multi-layer body surface electrode of claim 1 wherein the first layer comprises an adhesive material.

5. The multi-layer body surface electrode of claim 1 further comprising a cable comprising a splayed end, the splayed end adhered between and contacting the first layer and the second layer.

6. A multi-layer body surface electrode kit comprising:
a plurality of multi-layer body surface electrodes, each multi-layer body surface electrode consisting of three flat, disk-shaped layers, the layers consisting of:
a first layer having a first, uniform diameter and comprising a sidewall that extends between a top surface of the first layer and a continuous planar bottom surface of the first layer;
a second layer having a second diameter and comprising an electrically conductive material, the second layer further comprising a continuous planar top surface and a continuous planar bottom surface; and
a third layer having a third diameter and comprising an electrically conductive adhesive that forms a continuous planar top surface, wherein the second layer is positioned between the first layer and the third layer, and wherein the second diameter is smaller than the first diameter and the third diameter, wherein the first layer continuous planar bottom surface contacts the second layer continuous planar top surface and covers the entirety of the second layer continuous planar top surface, and wherein the third layer continuous planar top surface contacts the second layer continuous planar bottom surface and covers the entirety of the second layer continuous planar bottom surface such that the electrically conductive adhesive of the third layer is in direct contact with the electrically conductive material of the second layer and also extends radially outward beyond a periphery of the electrically conductive material of the second layer;

wherein the first, second, and third layers are configured such that the first and third layers form a barrier around the second layer configured to facilitate reducing a potential of impedance changes when adhered to the patient's skin.

7. The multi-layer body surface electrode kit of claim 6 wherein the first diameter is larger than the third diameter.

8. The multi-layer body surface electrode kit of claim 6 wherein the first layer comprises an adhesive material.

9. The multi-layer body surface electrode kit of claim 8 wherein the first layer comprises an adhesive foam configured to adhere to a patient's skin at least on a bottom surface thereof.

10. The multi-layer body surface electrode kit of claim 6 wherein the second layer comprises an electrically conductive silver carbon film.

11. The multi-layer body surface electrode kit of claim 6 wherein the first and second layers are configured to receive a cable therebetween for conducting a signal to the multi-layer body surface electrode.

12. A medical positioning system comprising:
a plurality of multi-layer body surface electrodes, each multi-layer body surface electrode consisting of three flat, disk-shaped layers, the layers consisting of:
a first layer having a first, uniform diameter and including adhesive foam configured to adhere to a patient's skin at least on a bottom surface thereof, the first layer further including a sidewall that extends between a top surface of the first layer and a continuous planar bottom surface of the first layer;
a second layer having a second diameter and including an electrically conductive material, the second layer further comprising a continuous planar top surface and a continuous planar bottom surface; and
a third layer having a third diameter and including an electrically conductive adhesive that forms a continuous planar top surface, wherein the second diameter is smaller than the first diameter and the third diameter, wherein the first diameter is larger than the third diameter, wherein the second layer is positioned between the first layer and the third layer, wherein the first layer continuous planar bottom surface contacts the second layer continuous planar top surface and covers the entirety of the second layer continuous planar top surface, and wherein the third layer continuous planar top surface contacts the second layer continuous planar bottom surface and covers the entirety of the second layer continuous planar bottom surface such that the electrically conductive adhesive of the third layer is in direct contact with the electrically conductive material of the second layer and also extends radially outward beyond a periphery of the electrically conductive material of the second layer;
wherein the first, second, and third layers are configured such that the first and third layers form a barrier around the second layer configured to facilitate reducing a potential of impedance changes when adhered to the patient's skin;
a plurality of cables each having a first end positioned between the first layer and second layer of each of the plurality of multi-layer body surface electrodes, the plurality of cables configured to transmit signals from each of the multi-layer body surface electrodes; and
a device coupled to a second end of each of the plurality of cables and configured to receive the signals and determine a location of a medical device within the patient based on the signals.

13. The multi-layer body surface electrode of claim 1 wherein the electrically conductive adhesive of the third layer is an electrically conductive adhesive gel.

* * * * *